United States Patent [19]

Kajihara et al.

[11] Patent Number: 5,326,870

[45] Date of Patent: Jul. 5, 1994

[54] SUBSTITUTED SULFONAMIDE DERIVATIVE AND A PHARMACEUTICAL COMPOSITION COMPRISING THE SAME

[75] Inventors: Akiro Kajihara, Niiza; Toshio Asano, Mishima, both of Japan

[73] Assignee: Asahi Kasei Kogyo Kabushiki Kaisha, Osaka, Japan

[21] Appl. No.: 927,493

[22] PCT Filed: Feb. 13, 1992

[86] PCT No.: PCT/JP92/00146

§ 371 Date: Sep. 29, 1992

§ 102(e) Date: Sep. 29, 1992

[87] PCT Pub. No.: WO92/14712

PCT Pub. Date: Sep. 3, 1992

[30] Foreign Application Priority Data

Feb. 13, 1991 [JP] Japan .................................. 3-19761

[51] Int. Cl.$^5$ .................. C07D 401/12; C07D 243/08; C07D 295/067; C07D 295/104
[52] U.S. Cl. ...................................... 540/575; 544/363
[58] Field of Search ................ 544/363; 514/253, 218; 540/575

[56] References Cited

U.S. PATENT DOCUMENTS

| | | | |
|---|---|---|---|
| 4,456,757 | 6/1984 | Hidaka et al. | 546/139 |
| 4,525,589 | 6/1985 | Hidaka et al. | 544/128 |
| 4,560,755 | 12/1985 | Hidaka et al. | 544/363 |
| 4,634,770 | 1/1987 | Hidaka et al. | 546/145 |
| 4,678,783 | 7/1987 | Hidaka et al. | 514/218 |
| 4,709,032 | 11/1987 | Hidaka et al. | 544/363 |
| 4,798,897 | 1/1989 | Hidaka et al. | 546/139 |
| 5,245,034 | 9/1993 | Hidaka et al. | 540/575 |

FOREIGN PATENT DOCUMENTS

| | | |
|---|---|---|
| 121278 | 7/1983 | Japan . |
| 60-81168 | 5/1985 | Japan . |
| 126026 | 6/1986 | Japan . |
| 130268 | 6/1986 | Japan . |
| 2-73067 | 3/1990 | Japan . |
| 2-73068 | 3/1990 | Japan . |
| 2-184673 | 7/1990 | Japan . |

OTHER PUBLICATIONS

Anri Morikawa et al., "5-Isoquinolinesulfonamide Derivatives. 1. Synthesis and Vasodilatory Activity of N-(2-Guanidinoethyl)-5-isoquinolinesulfonamide Derivatives", *J. Med. Chem.*, vol. 32, pp. 42-50, (1989).
W. Kreutner et al., "The Effect of leukotriene antagonists, lipoxygenase inhibitors and selected standards on leukotriene-mediated allergic bronchospasm in guinea pigs", *Agents and Actions*, vol. 28, pp. 173-184 (1989).
Richard W. Chapman et al., "Antibronchoconstrictor Activity of the Intracellular Calcium Antagonist HA 1004 in Guinea Pigs", *Pharmacology* 27: pp. 187-194 (1988).
Anri Morikawa et al., "5-Isoquinolinesulfonamide Derivatives. III. Synthesis and Vasodilatory Activity of 1-(5-Isoquinoline-sulfonyl) piperazine Derivatives", *Chem. Pharm. Bull.* vol. 40, No. 3, pp. 770-773 (1992).

*Primary Examiner*—C. Warren Ivy
*Assistant Examiner*—D. Margaret M. Mach
*Attorney, Agent, or Firm*—Finnegan, Henderson, Farabow, Garrett & Dunner

[57] ABSTRACT

Disclosed is a substituted sulfonamide derivative represented by formula (I) or a pharmaceutically acceptable acid addition salt thereof

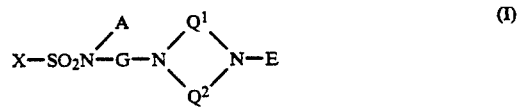

wherein A represents a hydrogen atom or an alkyl group, G represents a methylene group or an alkylene group, $Q^1$ represents an ethylene group, $Q^2$ represents an ethylene group or a trimethylene group, E represents an alkyl group or a group represented by a formula selected from formula (II-a) and (II-b)

$$-G-J-Z \qquad \text{(II-a),}$$

$$-G-Z \qquad \text{(II-b)}$$

wherein G is as defined above, J represents an oxygen atom, a sulfur atom or a nitrogen atom, and Z represents an aryl group unsubstituted or substituted with an alkyl group or an alkoxy group, or a heterocyclic group, and X represents a quinolyl group, an isoquinolyl group, a benzothiazolyl group or a quinazolin-4-on group. The substituted sulfonamide derivative and pharmaceutically acceptable acid addition salt thereof affect the bronchial smooth muscle of a mammal, and are useful as an active ingredient of a pharmaceutical composition for the prevention and treatment of respiratory diseases, such as asthma.

5 Claims, No Drawings

SUBSTITUTED SULFONAMIDE DERIVATIVE AND A PHARMACEUTICAL COMPOSITION COMPRISING THE SAME

TECHNICAL FIELD

The present invention relates to a novel substituted sulfonamide derivative and a pharmaceutical composition comprising the same. More particularly, the present invention is concerned with a substituted sulfonamide derivative, in which the S atom of a sulfonamide moiety has, bonded thereto, a quinolyl group, an isoquinolyl group, a benzothiazolyl group or a quinazolin-4-on group and the N atom of the sulfonamide moiety has, bonded thereto via a methylene group or an alkylene group, a piperazinyl group or a homopiperazinyl group, or an acid addition salt of the substituted sulfonamide derivative. The substituted sulfonamide derivative or acid addition salt thereof according to the present invention affects the bronchial smooth muscle of a mammal and is useful as an active ingredient of a pharmaceutical composition for the prevention and treatment of respiratory diseases, such as asthma. The present invention also relates to a pharmaceutical composition comprising the above-mentioned novel substituted sulfonamide derivative or acid addition salt thereof as an active ingredient.

BACKGROUND ART

Various compounds have been proposed as a drug for the treatment of respiratory diseases, such as a vasodilator, a cerebral circulation ameliorator and a drug for the treatment of angina and the like. In this connection, reference may be made to, for example, European Patent No. 0061673 (corresponding to U.S. Pat. No. 4,456,757, U.S. Pat. No. 4,560,755, U.S. Pat. No. 4,525,589, Japanese Patent Application Laid-Open Specification No. 57-156463, Japanese Patent Application Laid-Open Specification No. 57-200366, Japanese Patent Application Laid-Open Specification No. 58-121278, and Japanese Patent Application Laid-Open Specification No. 58-121279), European Patent No. 0109023 (corresponding to U.S. Pat. No. 4,634,770, U.S. Pat. No. 4,709,023, Japanese Patent Application Laid-Open Specification No. 59-93054, and Japanese Patent Application Laid-Open Specification No. 60-81168), U.S. Pat. No. 4,678,783 (corresponding to Japanese Patent Application Laid-Open Specification No. 61-152658 and Japanese Patent Application Laid-Open Specification No. 61-227581), U.S. Pat. No. 4,798,897 (corresponding to Japanese Patent Application Laid-Open Specification No. 62-103066 and Japanese Patent Application Laid-Open Specification No. 62-111981), Journal of Medicinal Chemistry, 32, 42–50 (1989), Agents Actions 28 (3–4), 173–184 (1989), and Pharmacology, 37 (3), 187–194 (1988).

In Japanese Patent Application Laid-Open Specification No. 2-184673, sulfonamides were proposed as a drug for the treatment of respiratory diseases. In Japanese Patent Application Laid-Open Specification Nos. 2-073067 and 2-073068, quinolines and isoquinolines were proposed as a drug for the prevention and treatment of respiratory diseases.

It is known in the art that N-(2-aminoethyl)-N-hexyl-5-isoquinolinesulfonamide and 1-(5-isoquinolinesulfonyl)-3-aminopiperidine disclosed in U.S. Pat. No. 4,798,897 and N-(2-guanidinoethyl)-5-isoquinolinesulfonamides disclosed in Agents Actions, vol. 28, No. 3–4, pp 173–184 (1989), Pharmacology, vol. 37, No. 3, pp 187–194 (1988) and European Patent No. 0109023 have not only a vasodilating effect but also a bronchodilating effect. It is also known in the art that N-[2-3,4-methylenedioxybenzylamino)ethyl]-8-chloro-5-quinolinesulfonamides have a brochodilating effect. However, the vasodilating and bronchodilating effects of the above compounds are not satisfactory.

Bronchodilators, such as xanthine type medicines and β-receptor stimulants, are widely used as a clinical, therapeutic agent for the treatment of respiratory diseases, such as asthma. As a representative example of the xanthine type medicines, aminophylline can be mentioned. Further, as a representative example of the β-receptor stimulants, isoproterenol can be mentioned However, these xanthine type medicines and β-receptor stimulants have side effects on the heart and the like, and an intractable asthma which is not remitted by these medicines has emerged. Therefore, these medicines do not always satisfy the demand of clinicians.

In these situations, the present inventors have made extensive and intensive studies with a view toward developing a drug which is more useful for prevention and treatment of respiratory diseases, such as asthma. As a result, it has been found that a specific substituted sulfonamide derivative, in which the S atom of a sulfonamide moiety has, bonded thereto, a quinolyl group, an isoquinolyl group, a benzothiazolyl group or a quinazolin-4-on group and the N atom of the sulfonamide moiety has, bonded thereto via a methylene group or an alkylene group, a piperazinyl group or a homopiperazinyl group, and an acid addition salt thereof, have strong bronchodilating activity. Based on this finding, the present invention has been completed.

Accordingly, it is an object of the present invention to provide a substituted sulfonamide derivative or an acid addition salt thereof which has an excellent activity to inhibit bronchoconstriction so that it is useful as an active ingredient of a drug for the prevention and treatment of respiratory diseases, such as asthma.

It is another object of the present invention to provide a pharmaceutical composition comprising the above-mentioned sulfonamide derivative or acid addition salt thereof as an active ingredient, which has excellent bronchoconstriction inhibiting activity so that it is useful as a drug for the prevention and treatment of respiratory diseases, such as asthma.

The foregoing and other objects, features and advantages of the present invention will be apparent from the following detailed description and appended claims.

DISCLOSURE OF THE INVENTION

According to the present invention, there is provided a substituted sulfonamide derivative represented by formula (I) or a pharmaceutically acceptable acid addition salt thereof

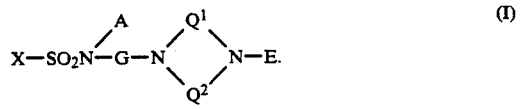

In the above formula (I), A represents a hydrogen atom or an alkyl group having 1 to 6, preferably 1 to 3 carbon atoms. A hydrogen atom is particularly preferred. Representative examples of such alkyl groups include a methyl group and an ethyl group.

In the above formula (I), G represents a group selected from a methylene group and an alkylene group having 2 to 6 carbon atoms, which are each unsubstituted or each have at least one carbon-bonded hydrogen atom substituted with an alkyl group having 1 to 6 carbon atoms or with a hydroxyl group. Of these, an ethylene group is particularly preferred.

In the above formula (I), $Q^1$ represents an ethylene group which is unsubstituted or has at least one carbon-bonded hydrogen atom substituted with an alkyl group having 1 to 6 carbon atoms. $Q^2$ represents a group selected from an ethylene group and a trimethylene group, which are each unsubstituted or each have at least one carbon-bonded hydrogen atom substituted with an alkyl group having 1 to 6 carbon atoms. Of these, it is particularly preferred that $Q^1$ represent an ethylene group and $Q^2$ represent an ethylene group or a trimethylene group.

In the above formula (I), E represents a group selected from a straight chain or branched alkyl group having 1 to 6 carbon atoms, a group represented by formula (II-a) and a group represented by formula (II-b),

- G - J - Z  (II-a),

- G - Z  (II-b)

which are each unsubstituted or each have at least one carbon-bonded hydrogen atom substituted with an alkyl group having 1 to 6 carbon atoms or with a hydroxyl group.

It is preferred that E represent a group of formula (II-a) or formula (II-b). In the formulae (II-a) and (II-b), G is as defined above, and J represents an oxygen atom, a sulfur atom or a nitrogen atom. Of these, it is particularly preferred that G represent an ethylene group or a trimethylene group and J represent an oxygen atom. Z represents an aryl group having 5 to 10 carbon atoms which is unsubstituted or has at least one carbon-bonded hydrogen atom substituted with an alkyl group having 1 to 6, preferably 1 to 3 carbon atoms, an alkoxy group having 1 to 6, preferably 1 to 3 carbon atoms or a halogen atom, or a heterocyclic group having 1 to 5 carbon atoms and having 1 to 4 heteroatoms, said heteroatoms being at least one atom selected from an oxygen atom, a sulfur atom and a nitrogen atom, with the proviso that when said heteroatom is an oxygen atom, said oxygen atom is not bonded to the above-mentioned G or J. Of these, it is particularly preferred that Z represent a phenyl group which is unsubstituted or has at least one carbon-bonded hydrogen atom substituted with an alkyl group having 1 to 6 carbon atoms, an alkoxy group having 1 to 6 carbon atoms or a halogen atom. Representative examples of such alkyl groups having 1 to 6 carbon atoms include a methyl group and an ethyl group. Representative examples of such alkoxy groups having 1 to 6 carbon atoms include a methoxy group and an ethoxy group. Representative examples of halogen atoms include fluorine, chlorine, bromine and iodine atoms. It is particularly preferred that the heterocyclic group is a pyridyl group.

In the above formula (I), X represents a group represented by a formula selected from the following formulae:

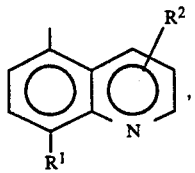  (III-a)

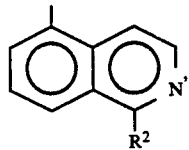  (III-b)

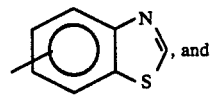  , and  (III-c)

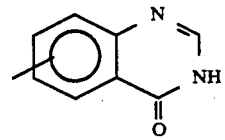  (III-d)

wherein $R^1$ represents a hydrogen atom, a halogen atom or an alkyl group having 1 to 6 carbon atoms, and $R^2$ represents a hydrogen atom or a hydroxyl group, with the proviso that when $R^2$ is a hydroxyl group and bonded to the 2-position of formula (III-a), said group of formula (III-a) is a carbostyril group.

Of the groups represented by the above formulae, a quinolyl group of formula (III-a) and an isoquinolyl group of formula (III-b) are particularly preferred. In the quinolyl group, it is particularly preferred that substituent $R^1$ represent a halogen atom. Representative examples of such halogen atoms include fluorine, chlorine, bromine, and iodine atoms.

Examples of substituted sulfonamide derivatives represented by formula (I) according to the present invention include the following compounds:

(1) 1-(8-chloro-5-quinolinesulfonylaminoethyl)-4-[3-(phenylthio)propyl]piperazine
(2) 1-(8-chloro-5-quinolinesulfonylaminoethyl)-4-[3-(phenoxy)propyl]piperazine
(3) 1-(8-chloro-5-quinolinesulfonylaminoethyl)-4-[3-(phenylthio)propyl]homopiperazine
(4) 1-(8-chloro-5-quinolinesulfonylaminoethyl)-4-[3-(phenoxy)propyl]homopiperazine
(5) 1-(8-chloro-5-quinolinesulfonylaminoethyl)-4-[3-(phenoxy)ethyl]piperazine
(6) 1-(8-chloro-5-quinolinesulfonylaminoethyl)-4-[3-(phenoxy)butyl]piperazine
(7) 1-(8-fluoro-5-quinolinesulfonylaminoethyl)-4-[3-(phenoxy)propyl]piperazine
(8) 1-(8-methyl-5-quinolinesulfonylaminoethyl)-4-[3-(phenoxy)propyl]piperazine
(9) 1-(5-quinolinesulfonylaminoethyl)-4-[3-(phenoxy)propyl]piperazine
(10) 1-(8-chloro-5-quinolinesulfonylaminoethyl)-4-[3-(4-fluorophenoxy)propyl]homopiperazine
(11) 1-(8-chloro-5-quinolinesulfonylaminoethyl)-4-[3-(4-methoxyphenoxy)propyl]homopiperazine
(12) 1-(8-chloro-5-quinolinesulfonylaminoethyl)-4-[3-(4-methylphenoxy)propyl]homopiperazine

(13) 1-(8-chloro-5-quinolinesulfonylaminopropyl)-4-[3-(phenoxy)propyl]piperazine
(14) 1-(8-chloro-5-quinolinesulfonyl)-N-methylaminoethyl)-4-[3-(phenoxy)propyl]piperazine
(15) 1-(8-chloro-5-quinolinesulfonylaminoethyl)-4-[3-$\beta$-naphthoxy)propyl]piperazine
(16) 1-(8-chloro-5-quinolinesulfonylaminoethyl)-3-methyl-4-[3-(phenoxy)propyl]piperazine
(17) 1-(8-chloro-5-quinolinesulfonylaminoethyl)-4-(propyl)piperazine
(18) 1-(8-chloro-5-quinolinesulfonylaminoethyl)-4-[2-(methyl)propyl]piperazine
(19) 1-(8-chloro-5-quinolinesulfonylaminoethyl)-4-[3-(hydroxy)propyl]piperazine
(20) 1-(6-benzothiazolsulfonylaminoethyl)-4-[3-(phenoxy)propyl]piperazine
(21) 1-(6-quinazolin-4-onsulfonylaminoethyl)-4-[3-(phenoxy)propyl]piperazine
(22) 1-(5-isoquinolinesulfonylaminoethyl)-4-[3-(phenoxy)propyl]piperazine
(23) 1-(8-chloro-5-carbostyrilsulfonylaminoethyl)-4-[3-(phenoxy)propyl]piperazine dihydrochloride
(24) 1-(1-hydroxy-5-isoquinolinesulfonylaminoethyl)-4-[3-(phenoxy)propyl]piperazine dihydrochloride
(25) 1-(8-chloro-5-quinolinesulfonylaminoethyl)-4-[3-(3-pyridyl)propyl]piperazine.

Further, according to the present invention, there is also provided an acid addition salt of the substituted sulfonamide derivative represented by the abovementioned formula (I). This salt is a pharmacologically acceptable, non-toxic salt. Examples of salts include salts with inorganic acids, such as hydrochloric acid, hydrobromic acid, phosphoric acid and sulfuric acid, and organic acids, such as acetic acid, citric acid, tartaric acid, lactic acid, succinic acid, fumaric acid, maleic acid and methanesulfonic acid.

The substituted sulfonamide derivative of the present invention can be produced by various methods and is not particularly limited. For example, there can be mentioned a method in which a sulfonic acid which has the above-mentioned substituent X (where $R^2$ represents a hydrogen atom) is reacted with thionyl chloride or the like to convert the sulfonic acid group to a sulfonyl chloride group, thereby obtaining a sulfonyl chloride compound, and then, the obtained sulfonyl chloride compound is reacted with an amine represented by the following formula:

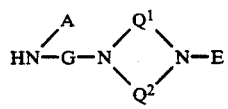

(IV)

wherein A, G, $Q^1$, $Q^2$ and E are as defined above for formula (I).

In the case where $R^2$ in the above-mentioned substituent X represents a hydroxyl group, the substituted sulfonamide derivative of the present invention can be produced by a method in which a sulfonic acid which has a substituent (which corresponds to substituent X but has a chlorine atom at the $R^2$ position thereof) is reacted with thionyl chloride or the like to convert the sulfonic acid group to a sulfonyl chloride group, thereby obtaining a sulfonyl chloride compound, and then, the sulfonyl chloride compound is reacted with an amine represented by the above formula (IV), followed by hydrolysis with an inorganic acid or an organic acid. The acid addition salt of the substituted sulfonamide derivative according to the present invention can readily be produced by reacting the substituted sulfonamide derivative obtained by the method mentioned above with an inorganic acid or an organic acid. On the other hand, when the compound is obtained in an acid addition salt form by the above-mentioned methods (in which a sulfonic acid is used as a starting material), the corresponding compound in a free form can easily be formed by treatment with an alkali.

Hereinbelow, representative examples of methods for producing the substituted sulfonamide derivative and acid addition salt thereof according to the present invention will be described in detail. (Method 1): Production of a substituted sulfonamide derivative represented by formula (I), wherein $R^2$ of X is a hydrogen atom In accordance with the following formula (V), an X-substituted sulfonic acid of formula (VI) is reacted with thionyl chloride in the presence of a catalytically effective amount (usually 0.5 to 5 % by volume based on the amount of thionyl chloride) of N,N-dimethylformamide, thereby obtaining an X-substituted sulfonyl chloride of formula (VII) in accordance with the route of formula (V):

wherein X has the same meaning as defined for formula (I) with the proviso that $R^2$ represents a hydrogen atom.

The compound of formula (VII) is then reacted with the compound of formula (IV), thereby obtaining the desired compound represented by formula (I) wherein $R^2$ represents a hydrogen atom.

The reaction between the compound of formula (VII) and the compound of formula (IV) may be carried out in the presence or absence of an acid acceptor. Examples of acid acceptors which may be employed include alkali metal compounds, such as sodium hydrogencarbonate, sodium hydroxide, potassium carbonate, sodium carbonate and sodium methylate, and organic tertiary amines, such as pyridine, trimethylamine and triethylamine.

The reaction between the compound of formula (VII) and the compound of formula (IV) may be carried out in a solvent. Examples of solvents which may be employed include halogenated hydrocarbons, such as dichloromethane and chloroform; ethers such as tetrahydrofuran, dioxane and diethyl ether; dimethyl sulfoxide; N,N-dimethylformamide; acetonitrile; water; and the like. These solvents may be used individually or in a mixture.

The amount of the compound of formula (IV) may be in the range of from 1 to 20 mols, preferably from 1 to 10 mols per mol of the compound of formula (VII). It is more preferable that the amount of the compound of formula (IV) be in the range of from 2.5 to 5 mols per mol of the compound of formula (VII) when an acid acceptor is absent, and in the range of from 1 to 3 mols per mol of the compound of formula (VII) when an acid acceptor is present.

The reaction temperature is generally in the range of from $-30°$ to $120°$ C., preferably $-20°$ to $50°$ C. The reaction time is generally 0.5 to 48 hours, preferably 0.5 to 6 hours.

(Method 2): Production of an acid addition salt from the substituted sulfonamide derivative obtained in Method 1

The compound obtained in Method 1 is dissolved in an alcohol, such as methanol and ethanol, to obtain a solution. Then, an equivalent or several fold amount of an acid is added to the solution to form an acid addition salt. Examples of such acids include inorganic acids, such as hydrochloric acid, hydrobromic acid, phosphoric acid and sulfuric acid, and organic acids, such as acetic acid, citric acid, tartaric acid, lactic acid, succinic acid, fumaric acid, maleic acid and methanesulfonic acid. (Method 3): Production of a substituted sulfonamide derivative represented by formula (I), wherein $R^2$ of X is a hydroxyl group A sulfonic acid substituted with X wherein $R^2$ represents a chlorine atom is reacted and treated in substantially the same manner as in Method 1, thereby obtaining a compound represented by the following formula (VIII):

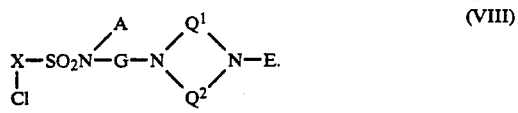

(VIII)

Hydrolysis of the compound of formula (VIII) with an aqueous solution of an inorganic acid gives the desired compound in which $R^2$ represents a hydroxyl group, the desired compound being in the form of an acid addition salt.

Representative examples of inorganic acids include hydrochloric acid, sulfuric acid and hydrobromic acid. The concentration of the inorganic acid in the aqueous solution is preferably in the range of from 0.25 to 10 mole/liter.

The reaction temperature is generally in the range of from 50° to 100° C., and the reaction time is generally in the range of from 2 to 6 hours.

The substituted sulfonamide derivative and pharmaceutically acceptable acid addition salt thereof according to the present invention exert an excellent bronchial smooth muscle relaxation action. Accordingly, these are substances useful for prevention and treatment of respiratory organ diseases, such as asthma.

Accordingly, in another aspect of the present invention, there is provided a pharmaceutical composition comprising a substituted sulfonamide derivative represented by formula (I) or a pharmaceutically acceptable acid addition salt thereof, and at least one pharmaceutically acceptable carrier or diluent.

Examples of carriers which may be employed include vehicles, such as lactose, sucrose, glucose, starch and crystalline cellulose; binders, such as hydroxypropyl cellulose, carboxymethyl cellulose, starch, gum arabic, gelatin, glucose, sucrose, tragacanth and sodium alginate; disintegrators, such as carboxymethyl cellulose, starch and calcium carbonate; lubricants, such as magnesium stearate, refined tarc, stearic acid and calcium stearate; additives such as lecithine, soybean oil and glycerin; and the like. In the case where the compounds of the present invention are formulated into an inhalant, polychloromonofluoromethane or the like may be used as a solvent.

Further, the compound of the present invention may be used in combination with other drugs, depending on the symptoms of a patient. For example, the compound may be used in combination with other bronchodilators, antiallegic agents, steroids, expectorants and antibiotics.

When the compound of the present invention is administered to human, the compound may be orally administered in the form of a tablet, powder, granule, capsule, sugar-coated tablet, suspension and syrup, or parenterally administered in the form of a solution or suspension for injection, cream and spray. The dose is varied depending on the age, weight, condition, etc. of the patient. However, the dose may generally be in the range of from 3 to 300 mg per day for an adult. The daily dose may be administered at one time, or it may also be divided into 2 or 3 portions and these portions are administered at intervals. The administration is generally continued for a period of from several days to 2 months. The daily dose and the administration period are varied to some extent, depending on the condition of the patient.

The efficacy of the substituted sulfonamide derivative according to the present invention was assayed by the effect thereof on the supression of the histamine-induced constriction of the trachea of a guinea pig. As a result, the following was confirmed.

That is, in the in vivo experiment on the trachea of a guinea pig, 1-(8-chloro-5-quinolinesulfonylaminoethyl)-4-[3-(phenylthio)propyl]piperazine (1) and 1-(8-chloro-5-quinolinesulfonylaminoethyl)-4-[3-(phenoxy) propyl]-piperazine (2), each intravenously administered in an amount of 0.1 mg/kg, respectively suppressed 82% and 88% of histamine-induced bronchoconstriction. By contrast, intravenous administration of 1 mg/kg of each of aminophylline and comparative compound (1) described later which were used as controls, respectively suppressed only 5% and 18% of histamine-induced bronchoconstriction.

As described above, the substituted sulfonamide derivative of the present invention exhibits an excellent bronchial smooth muscle relaxation activity, showing that it is a useful substance as a medicine for the prevention and treatment of respiratory organ diseases, such as asthma.

BEST MODE FOR CARRYING OUT THE INVENTION

In the following Examples, the respective yields of the desired compounds of the present invention as shown in Tables 1 to 8 are determined relative to the amount of a compound represented by formula (VI) above.

Hereinbelow, the present invention will be described in detail with reference to the following Examples but they should not be construed to be limiting the scope of the present invention.

EXAMPLE 1

To 14.2 g of 8-chloro-5-quinolinesulfonic acid were added 142 ml of thionyl chloride and 1.42 ml of dimethylformamide. The resultant mixture was heated under reflux for 3 hours and the thionyl chloride was removed by distillation under reduced pressure to obtain a residue. The thus obtained residue was dissolved in 100 ml of ice water and adjusted to a pH of 6 with a saturated aqueous sodium carbonate solution, followed by extraction with 100 ml of dichloromethane to obtain a dichloromethane phase. The dichloromethane phase was added dropwise to 100 ml of a dichloromethane solution containing 16.3 g of 1-(2-aminoethyl)-4-[3-(phenylthio)propyl]piperazine and 6.5 g of triethylamine over 30 minutes while cooling with ice. The resultant mixture was stirred at a temperature of 15° C. to 20° C. for 2 hours to carry out a reaction. After completion of the reaction, the resultant mixture was washed with 200 ml of water and dried over anhydrous magnesium sulfate. Then, solvent removal was conducted by distillation under reduced pressure to obtain a residue. The thus obtained residue was subjected to purification by means of a column for chromatography packed with 250 g of silica gel (Wakogel C-200, manufactured by Wako Pure Chemical Industries, Ltd., Japan), using a mixed solvent comprised of methanol and chloroform (2% methanol) as an eluent, to thereby obtain 21.2 g of 1-(8-chloro-5-quinolinesulfonylaminoethyl)-4-[3-(phenylthio)propyl]-piperazine (1) (yield: 72%).

NMR spectrum (δppm) (CDCl$_3$/CD$_3$OD): 1.7–2.5(14H), 2.8–3.0(2H), 3.8–4.0(2H), 6.6–8.2(8H), 8.9–9.2(2H).

Mass spectrum (m/e): 505.

EXAMPLES 2 to 17

Substantially the same procedure as in Example 1 was repeated, except that, in place of 1-(2-aminoethyl)-4-[3-(phenylthio)propyl]-piperazine, individual use was made of 1-(2-aminoethyl)-4-[3-(phenoxy)propyl]piperazine,
1-(2-aminoethyl)-4-[3-(phenylthio)propyl]homopiperazine,
1-(2-aminoethyl)-4-[3-(phenoxy)propyl]homopiperazine,
1-(2-aminoethyl)-4-[3-(phenoxy)ethyl]piperazine,
1-(2-aminoethyl)-4-[3-(phenoxy)butyl]piperazine,
1-(2-aminoethyl)-4-[3-(fluorophenoxy)propyl]piperazine,
1-(2-aminoethyl)-4-[3-(4-methoxyphenoxy)propyl]piperazine,
1-(2-aminoethyl)-4-[3-(4-methylphenoxy)propyl]piperazine,
1-(3-aminopropyl)-4-[3-(phenoxy)propyl]piperazine,
1-[N-(methyl)-2-aminoethyl]-4-[3-(phenoxy)propyl]piperazine,
1-(2-aminoethyl) -4-[3-(β-(naphthoxy)propyl]piperazine,
1-(2-aminoethyl) -3-methyl-4-[3-(phenoxy)propyl)piperazine,
1-(2-aminoethyl) -4-(propyl)piperazine,
1-(2-aminoethyl) -4-[2-(methyl)propyl]piperazine,
1-(2-aminoethyl) -4-[3-(hydroxy)propyl]piperazine, and
1-(2-aminoethyl)-4-[3-(3-pyridyl)propyl]piperazine, to thereby obtain compounds (2), (3), (4), (5), (6), (10), (11), (12), (13), (14), (15), (16), (17), (18), (19) and (25), respectively.

The reaction conditions are shown in Tables 1 to 3, and the yields and analytical data of these compounds are shown in Tables 4 and 5.

TABLE 1

| | Amines used | | Reaction | |
|---|---|---|---|---|
| | Type | Amount (g) | temperature (°C.) | Time (hours) |
| Example 2 | H$_2$NCH$_2$CH$_2$N⟨piperazine⟩NCH$_2$CH$_2$CH$_2$—O—C$_6$H$_5$ | 15.4 | 15–20 | 2 |
| Example 3 | H$_2$NCH$_2$CH$_2$N⟨homopiperazine⟩NCH$_2$CH$_2$CH$_2$—S—C$_6$H$_5$ | 17.1 | 15–20 | 1 |
| Example 4 | H$_2$NCH$_2$CH$_2$N⟨homopiperazine⟩NCH$_2$CH$_2$CH$_2$—O—C$_6$H$_5$ | 16.2 | 15–20 | 2 |
| Example 5 | H$_2$NCH$_2$CH$_2$N⟨piperazine⟩NCH$_2$CH$_2$—O—C$_6$H$_5$ | 14.5 | 15–20 | 2 |
| Example 6 | H$_2$NCH$_2$CH$_2$N⟨piperazine⟩NCH$_2$CH$_2$CH$_2$CH$_2$—O—C$_6$H$_5$ | 16.2 | 15–20 | 2 |
| Example 7 | H$_2$NCH$_2$CH$_2$N⟨piperazine⟩NCH$_2$CH$_2$CH$_2$—O—C$_6$H$_4$—F | 16.4 | 15–20 | 1 |

TABLE 2

| | Amines used | Amount (g) | Reaction temperature (°C.) | Time (hours) |
|---|---|---|---|---|
| | Type | | | |
| Example 8 | H₂NCH₂CH₂N(piperazine)NCH₂CH₂CH₂—O—C₆H₄—OMe | 17.1 | 15–20 | 2 |
| Example 9 | H₂NCH₂CH₂N(piperazine)NCH₂CH₂CH₂—O—C₆H₄—Me | 16.2 | 15–20 | 1 |
| Example 10 | H₂NCH₂CH₂CH₂N(piperazine)NCH₂CH₂CH₂—O—C₆H₅ | 16.2 | 15–20 | 1 |
| Example 11 | MeHNCH₃CH₂N(piperazine)NCH₂CH₂CH₂—O—C₆H₅ | 16.2 | 15–20 | 1 |
| Example 12 | H₂NCH₂CH₂N(piperazine)NCH₂CH₂CH₂—O—naphthyl | 18.4 | 15–20 | 1 |

TABLE 1

| | Amines used | Amount (g) | Reaction temperature (°C.) | Time (hours) |
|---|---|---|---|---|
| | Type | | | |
| Example 13 | H₂NCH₂CH₂N(2-Me-piperazine)NCH₂CH₂CH₂—O—C₆H₅ | 16.2 | 15–20 | 1 |
| Example 14 | H₂NCH₂CH₂N(piperazine)NCH₂CH₂CH₃ | 10.0 | 15–20 | 1 |
| Example 15 | H₂NCH₂CH₂N(piperazine)NCH₂CH(CH₃)₂ | 10.8 | 15–20 | 1 |
| Example 16 | H₂NCH₂CH₂N(piperazine)NCH₂CH₂CH₂OH | 10.9 | 15–20 | 1 |
| Example 17 | H₂NCH₂CH₂N(piperazine)NCH₂CH₂CH₂—(pyridyl) | 14.8 | 15–20 | 1 |

TABLE 4

| Compound No. | Yield (%) | Mass spectrum (m/e) | NMR spectrum (δ ppm) (CDCl₃/CD₃OD) |
|---|---|---|---|
| Example (2) | 63 | 489 | 1.7–2.6 (14H), 2.9–3.1 (2H) |

TABLE 4-continued

| Compound No. | Yield (%) | Mass spectrum (m/e) | NMR spectrum (δ ppm) (CDCl₃/CD₃OD) |
|---|---|---|---|
| 2 | | | 3.9–4.1 (2H) |

TABLE 4-continued

| Compound No. | Yield (%) | Mass spectrum (m/e) | NMR spectrum (δ ppm) (CDCl₃/CD₃OD) |
|---|---|---|---|
| Example 3 | (3) | 64 | 519 | 6.7–8.3 (8H), 9.0–9.2 (2H) 1.4–2.0 (2H), 2.1–3.1 (18H) |
| Example 4 | (4) | 66 | 503 | 7.0–8.3 (8H), 9.0–9.2 (2H) 1.3–2.1 (2H), 2.2–3.1 (18H) |
| Example 5 | (5) | 69 | 475 | 7.0–8.3 (8H), 9.0–9.2 (2H) 1.6–2.6 (12H), 2.9–3.1 (2H) 3.8–4.1 (2H) |
| Example 6 | (6) | 69 | 503 | 6.7–8.3 (8H), 9.0–9.2 (2H) 1.6–1.9 (4H), 2.0–2.5 (12H) 2.8–3.1 (2H), 3.8–4.0 (2H) |
| Example 7 | (10) | 71 | 507 | 6.6–8.2 (8H), 8.9–9.1 (2H) 1.6–2.6 (14H) 2.8–3.1 (2H), 3.8–4.0 (2H) |
| Example 8 | (11) | 71 | 519 | 6.6–8.2 (7H), 8.9–9.1 (2H) 1.6–2.6 (14H), 2.8–3.1 (2H) 3.7 (3H), 3.8–4.0 (2H) |
| Example 9 | (12) | 72 | 503 | 6.6–8.2 (7H), 8.9–9.1 (2H) 1.7–2.8 (17H), 2.8–3.1 (2H) 3.8–4.0 (2H) |
| Example 10 | (13) | 63 | 503 | 6.6–8.2 (7H), 8.9–9.2 (2H) 1.7–2.6 (14H), 2.9–3.1 (2H) 3.5–4.1 (4H) |

TABLE 5

| Compound No. | Yield (%) | Mass spectrum (m/e) | NMR spectrum (δ ppm) (CDCl₃/CD₃OD) |
|---|---|---|---|
| Example 11 | (14) | 58 | 503 | 1.7–2.6 (17H), 2.9–3.1 (2H) 3.9–4.1 (2H) |
| Example 12 | (15) | 54 | 541 | 6.7–8.3 (8H), 9.0–9.2 (2H) 1.5–2.7 (14H), 2.8–3.1 (2H) 3.8–4.1 (2H) |
| Example 13 | (16) | 66 | 503 | 6.7–8.4 (10H), 8.9–9.2 (2H) 1.6–2.6 (17H), 2.8–3.1 (2H) 3.9–4.1 (2H) |
| Example 14 | (17) | 73 | 397 | 6.7–8.4 (8H), 9.0–9.2 (2H) 0.7–1.7 (5H), 2.1–2.5 (12H) 2.9–3.3 (2H) |
| Example 15 | (18) | 68 | 411 | 7.5–8.3 (3H), 9.0–9.2 (2H) 0.6–1.9 (8H), 2.0–2.5 (12H) 2.8–3.3 (2H) |
| Example 16 | (19) | 49 | 413 | 7.6–8.2 (3H), 8.9–9.1 (2H) 1.6–2.6 (14H) 2.8–3.1 (2H), 3.8–4.0 (2H) |
| Example 17 | (25) | 67 | 474 | 7.6–8.2 (3H), 8.9–9.1 (2H) 1.5–2.8 (16H), 2.9–3.1 (2H) 7.0–8.5 (7H), 9.0–9.2 (2H) |

EXAMPLES 18 to 23

Substantially the same procedure as in Example 1 was repeated, except that 1-[3-(phenoxy)propyl]piperazine was used in place of 1-[3-(phenylthio)propyl]piperazine, and that 13.2 g of 8-fluoro-5-quinolinesulfonic acid, 13.0 g of 8-methyl-5-quinolinesulfonic acid, 12.2 g of 5-quinolinesulfonic acid, 12.5 g of 6-benzothiazolesulfonic acid, 13.2 g of 6-quinazolin-4-onsulfonic acid, and 12.2 g of 5-isoquinolinesulfonic acid were individually used in place of 8-chloro-5-quinolinesulfonic acid, to thereby obtain compounds (7), (8), (9), (20), (21) and (22), respectively.

The reaction conditions are shown in Table 6, and the yields and analytical data of these compounds are shown in Table 7.

TABLE 1

| | Amines used | | Reaction | |
|---|---|---|---|---|
| | Type | Amount (g) | temperature (°C.) | Time (hours) |
| Example 18 | 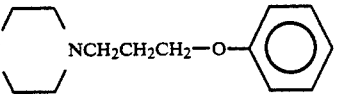 | 15.4 | 15–20 | 2 |
| Example 19 | 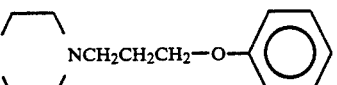 | 15.4 | 15–20 | 1 |
| Example 20 | 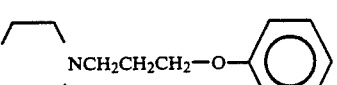 | 15.4 | 15–20 | 2 |
| Example 21 | 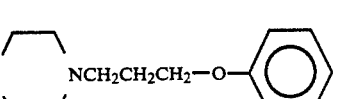 | 15.4 | 15–20 | 2 |
| Example 22 |  | 15.4 | 15–20 | 2 |

TABLE 1-continued

| | Amines used | | Reaction | |
|---|---|---|---|---|
| | Type | Amount (g) | temperature (°C.) | Time (hours) |
| Example 23 | H₂NCH₂CH₂N⟨piperazine⟩NCH₂CH₂CH₂—O—⟨phenyl⟩ | 15.4 | 15–20 | 1 |

TABLE 7

| Compound No. | Yield (%) | Mass spectrum (m/e) | NMR spectrum (δ ppm) (CDCl₃/CD₃OD) |
|---|---|---|---|
| Example 18 | (7) 62 | 472 | 1.7–3.1 (14H), 3.5–4.2 (4H) 6.8–8.4 (8H), 9.0–9.3 (2H) |
| Example 19 | (8) 67 | 468 | 1.7–3.1 (14H), 3.3–4.1 (7H) 6.8–8.4 (8H), 9.0–9.3 (2H) |
| Example 20 | (9) 68 | 454 | 1.7–3.1 (16H), 3.9–4.1 (2H) 6.8–8.4 (8H), 8.8–9.3 (3H) |
| Example 21 | (20) 70 | 460 | 1.6–2.6 (14H), 2.9–3.1 (2H) 3.8–4.1 (2H) 6.7–8.3 (8H), 9.0 (1H) |
| Example 22 | (21) 64 | 471 | 1.6–2.7 (14H), 2.8–3.1 (2H) 3.8–4.1 (2H) 6.6–9.0 (9H) |
| Example 23 | (22) 62 | 454 | 1.6–2.6 (14H), 2.8–3.1 (2H) 3.8–4.1 (2H) 6.6–8.7 (10H), 9.2 (1H) |

EXAMPLE 24

1.0 g of 1-(8-chloro-5-quinolinesulfonylaminoethyl)-4-[3-(phenylthio)propyl]piperazine obtained in Example 1 was dissolved in 10 ml of methanol, and to the resultant solution was added a 2-equivalent amount of an aqueous hydrochloric acid, followed by stirring for 10 minutes. Then, solvent removal was conducted by distillation under reduced pressure to obtain a residue. The thus obtained residue was subjected to recrystallization using a mixture of ethanol and ether to obtain 0.84 g of 1-(8-chloro-5-quinolinesulfonylaminoethyl)-4-[3-(phenylthio)propyl]piperazine dihydrochloride (yield: 73%).

Elementary analysis (%) of dihydrochloride of compound (1): Calculated: C: 49.87, H: 5.41, N: 9.69, Cl: 18.40. Found: C: 49.58, H: 5.46, N: 9.45, Cl: 18.28.

EXAMPLE 25

To 14.2 g of 1-chloro-5-isoquinolinesulfonic acid were added 142 ml of thionyl chloride and 1.42 ml of dimethylformamide. The resultant mixture was heated under reflux for 3 hours and the thionyl chloride was removed by distillation under reduced pressure to obtain a residue. The thus obtained residue was dissolved in 100 ml of ice water and adjusted to a pH of 6 with a saturated aqueous sodium carbonate solution, followed by extraction with 100 ml of dichloromethane to obtain a dichloromethane phase. The dichloromethane phase was dropwise added to 100 ml of a dichloromethane solution containing 15.4 g of 1-(2-aminoethyl)-4-[3-(phenoxy)propyl]piperazine and 6.5 g of triethylamine over 30 minutes while cooling with ice. The resultant mixture was stirred at a temperature of 15° C. to 20° C. for 2 hours to carry out a reaction. After completion of the reaction, the reaction mixture was washed with 200 ml of water and dried over anhydrous magnesium sulfate. Then, solvent removal was conducted by distillation under reduced pressure to thereby obtain a residue.

The thus obtained residue was subjected to purification by means of a column for chromatography packed with 250 g of silica gel (Wakogel C-200, manufactured by Wako Pure Chemical Industries, Ltd., Japan) using a mixed solvent of methanol and chloroform (2% methanol) as an eluent, to thereby obtain 19.6 g of 1-(1-chloro-5-isoquinolinesulfonylaminoethyl)-4-[3-(phenoxy) propyl]piperazine (yield: 69%).

To 19.6 g of 1-(1-chloro-5-isoquinolinesulfonylaminoethyl)-4-[3-(phenoxy)propyl]piperazine was added 200 ml of 6 mol/liter hydrochloric acid, and the resultant mixture was heated at 80° C. for 6 hours to obtain crystalline precipitate. The crystalline precipitate was filtered off and washed with 100 ml of ice water twice and then washed with 100 ml of ethanol twice, followed by drying, to thereby obtain 12.7 g of 1-(1-hydroxy-5-isoquinolinesulfonylaminoethyl)-4-[3-(phenoxy)-propyl]piperazine dihydrochloride (24) (yield: 58%).

NMR spectrum (δppm) (DMSO-d₆/CD₃OD): 1.7–2.7(14H), 2.8–3.0(2H), 3.8–4.2(2H), 6.6–7.8(8H), 8.0–8.8(2H), Mass spectrum (m/e): 470,

EXAMPLE 26

Substantially the same procedure as in Example 25 was repeated, except that 16.2 g of 2,8-dichloro-5-quinolinesulfonic acid was used in place of 1-chloro-5-isoquinolinesulfonic acid, to thereby obtain 18.2 g of 1-(2,8-dichloro-5-quinolinesulfonylaminoethyl)-4-[3-(phenoxy)propyl]piperazine (yield: 60%).

The thus-obtained compound was hydrolyzed in the same manner as in Example 25, thereby obtaining 11.2 g of 1-(8-chloro-5-carbostyrilsulfonylaminoethyl)-4-[3-(phenoxy)propyl]piperazine dihydrochloride (23) (yield: 56%).

NMR spectrum (δppm) (DMSO-d₆/CD₃OD): 1.7–2.5(14H), 2.8–3.0(2H), 3.8–4.0(2H), 6.6–8.7 (10H), Mass spectrum (m/e): 505

APPLICATION EXAMPLE 1

In vivo Test with Trachea

According to a modified Konzett-Rössler method [see J. Martinez et al, Bronchial Arterial Injections, vol. 33, p.295, (1961); and Masaaki Takai et al, Oyo Yakuri (Applied Pharmacology), vol. 17, p.345, (1979)], the efficacy of the compounds of the present invention was assayed on trachea in vivo. Compounds (1) to (22) used herein for testing were individually in the form of a dihydrochloride obtained in the same manner as in Example 24.

Urethane was intraperitoneally administered to male guinea pigs each weighing 350 to 500 g (Hartley strain, Kuroda monoclone) in an amount of 1.5 g/kg of body weight to anesthetize the guinea pigs. Then, cannulae were respectively inserted into the trachea and femoral veins of each guinea pig under urethane anesthesia and fixed. The inserted tracheal cannula was connected to a respirator for small animal (model 1683, manufactured by Harvard Co., Ltd.) and to a pneumotachometer (model MHF-1200, manufactured by Nihon Kohden Corp.) through a water-containing bottle positioned at a 10 cm height, and the respiration rate was measured.

Each of the above-mentioned compounds of the present invention was administered to guinea pigs through the femoral vein thereof in an amount of 0.1 mg/kg of body weight. Three minutes after the administration, histamine was administered to the guinea pigs through the femoral vein thereof in an amount of 20 μg/kg of body weight to thereby induce constriction of the trachea, and the suppression of the histamine-induced tracheal constriction, which was attained by each of the above-described compounds of the present invention, was determined. For comparison, the suppression of the histamine-induced tracheal constriction, which was exhibited by each of aminophylline and comparative compound (1), was determined in substantially the same manner as described above. As a solvent for each compound, physiological saline was used. The number of guinea pigs tested for each compound was 3.

The results are shown in Table 8.

TABLE 8

| Compound No. | Suppression of tracheal constriction (%) | Compound No. | Suppression of tracheal constriction (%) |
|---|---|---|---|
| (1) | 82 | (14) | 61 |
| (2) | 88 | (15) | 21 |
| (3) | 59 | (16) | 55 |
| (4) | 61 | (17) | 75 |
| (5) | 84 | (18) | 69 |
| (6) | 52 | (19) | 23 |
| (7) | 43 | (20) | 32 |
| (8) | 39 | (21) | 29 |
| (9) | 38 | (22) | 71 |
| (10) | 58 | (23) | 51 |
| (11) | 41 | (24) | 45 |
| (12) | 39 | (25) | 72 |
| (13) | 48 | Aminophylline | 5 |
|  |  | Comparative compound (1) | 18 |

Comparative compound (1):
N-[2-(4-methoxyphenethylamino)ethyl]-8-chloro-5-quinoline sulfoneamide hydrochloride Industrial Applicability Tha pharmaceutical composition containing as an active ingredient the novel substituted sulfonamide derivative or pharmaceutically acceptable acid addition salt thereof according to the present invention exhibits an excellent activity to inhibit the constriction of the bronchial smooth muscle of a mammal, and is useful as an effective medicine for the prevention and treatment of respiratory diseases, such as asthma.

We claim:

1. A substituted sulfonamide derivative represented by formula (I) or a pharmaceutically acceptable acid addition salt thereof

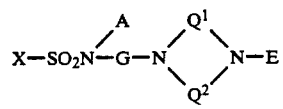
(I)

wherein A represents a hydrogen atom or an alkyl group having 1 to 6 carbon atoms; G represents a group selected from a methylene group and an alkylene group having 2 to 6 carbon atoms, which are each unsubstituted or each have at least one carbon-bonded hydrogen atom substituted with an alkyl group having 1 to 6 carbon atoms or with a hydroxyl group; $Q^1$ represents an ethylene group which is unsubstituted or has at least one carbon-bonded hydrogen atom substituted with an alkyl group having 1 to 6 carbon atoms; $Q^2$ represents a group selected from an ethylene group and a trimethylene group, which are each unsubstituted or each has at least one carbon-bonded hydrogen atom substituted with an alkyl group having 1 to 6 carbon atoms; E represents a group selected from a alkyl group having 1 to 6 carbon atoms, a group represented by formula (II-a) and a group represented by formula (II-b), which are each unsubstituted or each have at least one carbon-bonded hydrogen atom substituted with an alkyl group having 1 to 6 carbon atoms or with a hydroxyl group, -G-J-Z   (II-a), -G-Z   (II-b), wherein G is as defined above, J represents an oxygen atom, a sulfur atom or a nitrogen atoms, and Z represents an aryl group having 5 to 10 carbon atoms which is unsubstituted or has at least one carbon-bonded hydrogen atom substituted with an alkyl group having 1 to 6 carbon atoms, an alkoxy group having 1 to 6 carbon atoms or a halogen atom, or a pyridyl group, with the proviso that a nitrogen atom of said pyridyl group is not bonded to said G or said J; and X represents a group represented by a formula selected from the following formulae:

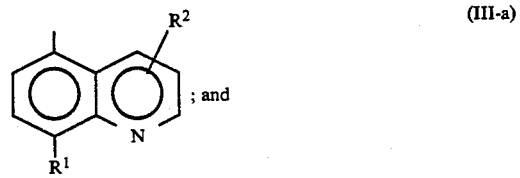
(III-a)

(III-b)

wherein $R^1$ represents a hydrogen atom, a halogen atom or an alkyl group having 1 to 6 carbon atoms, and $R^2$ represents a hydrogen atoms or a hydroxyl group, with a proviso that when $R^2$ is a hydroxyl group and bonded to the 2-position of formula (III-a), said group of formula (III-a) is a carbostyril group, with the proviso that when E represents said alkyl group or said group of formula (II-b), X represents said group of formula (III-a).

2. The substituted sulfonamide derivative or pharmaceutically acceptable acid addition salt thereof according to claim 1, wherein $Q^1$ is an ethylene group.

3. The substituted sulfonamide derivative or pharmaceutically acceptable acid addition salt thereof according to claim 1, wherein Z is a pyridyl group.

4. The substituted sulfonamide derivative or pharmaceutically acceptable acid addition salt thereof according to claim 1, wherein A is a hydrogen atom.

5. A pharmaceutical composition comprising a substituted sulfonamide derivative or pharmaceutically acceptable acid addition salt thereof according to claim 1, and at least one pharmaceutically acceptable carrier or diluent.

* * * * *

UNITED STATES PATENT AND TRADEMARK OFFICE
CERTIFICATE OF CORRECTION

PATENT NO. : 5,326,870
DATED : July 5, 1994
INVENTOR(S) : Akiro KAJIHARA et al.

It is certified that error appears in the above-identified patent and that said Letters Patent is hereby corrected as shown below:

Claim 1, column 18, line 10, delete "a" (second occurrence) and insert --an--.

Claim 1, column 18, line 21, delete "atoms" (second occurrence) and insert --atom--.

Claim 1, column 18, line 48, delete "atoms" and insert --atom--.

Signed and Sealed this

Eighteenth Day of October, 1994

Attest:

BRUCE LEHMAN

Attesting Officer    Commissioner of Patents and Trademarks